United States Patent [19]

Servas et al.

[11] Patent Number: 4,743,371

[45] Date of Patent: May 10, 1988

[54] BLOOD FILTER

[75] Inventors: Frank M. Servas, San Juan Capistrano; Robert F. Gremel, Huntington Beach; Timothy C. Ryan, Laguna Hills, all of Calif.

[73] Assignee: Shiley, Inc., Irvine, Calif.

[21] Appl. No.: 837,334

[22] Filed: Feb. 28, 1986

Related U.S. Application Data

[63] Continuation of Ser. No. 483,375, Apr. 8, 1983, abandoned.

[51] Int. Cl.⁴ .............................................. B01D 29/04
[52] U.S. Cl. ................................. 210/188; 210/315; 210/342; 55/178
[58] Field of Search .................. 55/178; 210/506, 503, 210/505, 507, 927, 315, 342, 188, 335

[56] References Cited

U.S. PATENT DOCUMENTS

| | | | |
|---|---|---|---|
| 3,003,643 | 10/1961 | Thomas | 210/491 |
| 3,246,767 | 4/1966 | Pall et al. | 210/506 X |
| 3,452,877 | 7/1969 | Mesek et al. | 210/491 |
| 3,507,395 | 4/1970 | Bentley | 210/143 |
| 3,511,382 | 5/1970 | Mesek | 210/489 |
| 3,573,158 | 3/1971 | Pall et al. | 162/131 |
| 3,593,854 | 7/1971 | Swank | 210/436 |
| 3,701,433 | 10/1972 | Krakauer et al. | 210/436 |
| 3,765,536 | 10/1973 | Rosenberg | 210/446 |
| 3,765,537 | 10/1973 | Rosenberg | 210/446 |
| 3,768,653 | 10/1973 | Brumfield | 210/188 |
| 3,770,129 | 11/1973 | Brumfield et al. | 210/232 |
| 3,827,562 | 8/1974 | Esmond | 210/304 |
| 3,891,416 | 6/1975 | Leonard et al. | 55/178 |
| 3,993,461 | 11/1976 | Leonard et al. | 210/321.1 X |
| 4,058,459 | 11/1977 | Griffin | 210/489 X |
| 4,073,732 | 2/1978 | Lauer et al. | 210/492 X |
| 4,087,363 | 5/1978 | Rosemeyer et al. | 210/927 X |
| 4,115,277 | 9/1978 | Swank | 210/321.1 X |
| 4,126,558 | 11/1978 | Luceyk | 210/927 X |
| 4,140,635 | 2/1979 | Esmond | 210/323.3 X |
| 4,157,965 | 6/1979 | Raible | 210/335 X |
| 4,157,967 | 6/1979 | Meyst et al. | 210/503 X |
| 4,157,968 | 6/1979 | Kronsbein | 210/489 |
| 4,164,468 | 8/1979 | Raible | 55/178 X |
| 4,203,847 | 5/1980 | Grandine | 210/500.2 X |
| 4,208,193 | 6/1980 | Munsch et al. | 55/178 X |
| 4,267,047 | 5/1981 | Henne | 210/500.2 X |
| 4,479,874 | 11/1984 | Rosenberg et al. | 210/446 X |
| 4,490,331 | 12/1984 | Steg, Jr. | 210/321.5 X |
| 4,568,367 | 2/1986 | Gremel et al. | 210/188 X |
| 4,599,093 | 7/1986 | Steg, Jr. | 210/188 X |

FOREIGN PATENT DOCUMENTS 2022434 5/1979 United Kingdom ............ 210/321.1

OTHER PUBLICATIONS

"Bentley Disposable Cardiotomy Reservoirs", 1979, Bentley Laboratories, Inc.
"Extracorporeal Answers Your Needs for a Total Cardiovascular System", 1982, Extracorporeal Inc.
"More Port Ability", William Harvey, a division of C. R. Bard, Inc.
"Be Selective (H-710F Filtered Cardiotomy Reservoir)," Bard Cardiopulmonary Division, C. R. Bard, Inc.
"Selecting a Filtered Cardiotomy Reservoir", Bard Cardiopulmonary International Division, C. R. Bard, Inc.
"Shily Cardiotomy Reservoir with Filter", 1980, Shiley, Inc.
D.A.C. Dideco Advanced Cardiotomy Reservoir, Distributed by Electromedics, Inc.
"How Does Travenol Design a Better Filtered Cardiotomy Reservoir"?, 1981, Travenal Laboratories, Inc.
"SciMed", SciMed Life Systems, Inc.
"Bentley Disposable Cardiotomy Reservoirs (Defoamer Filter)", 1981, Bentley Laboratories, Inc.
European Search Report, Aug. 14, 1984.

*Primary Examiner*—Frank Spear
*Attorney, Agent, or Firm*—Knobbe, Martens, Olson & Bear

[57] ABSTRACT

A filter device for a cardiotomy reservoir comprises multiple layers of concentric, tubular elements with a central passage for supply of blood, purified by passage through the device. A first, inner element for defoaming the blood comprises a porous sponge material within a second element comprising a depth filter medium for filtering the blood. The depth filter is surrounded by a third element of porous sponge material spacing apart the depth filter and the outer, fourth element, a fine-filter screen for removing substantially all remaining, undesirable particulate matter in the blood.

24 Claims, 2 Drawing Sheets

BLOOD FILTER

This application is a continuation of application Ser. No. 483,375, filed Apr. 8, 1983, now abandoned.

FIELD OF THE INVENTION

This invention is concerned with a filter unit for the purification of blood and especially with a cardiotomy reservoir containing the filter unit.

BACKGROUND OF THE INVENTION

Blood supplied to a patient must usually be purified by filtration to avoid jeopardizing the patient. The blood may be obtained from the patient during surgery when it is advantageous to store excess blood outside the body to facilitate the surgical procedure, or in blood conservation by scavenging the blood from the wound. Such blood is usually collected in a cardiotomy reservoir and purified there by passage through a filter unit within the reservoir. In cardiopulmonary bypass procedures where an extracorporeal blood circuit is generated and an oxygenator in the circuit takes over the function of the lungs, a cardiotomy reservoir commonly supplies purified blood to the oxygenator. The blood passing through the reservoir must not only be purified of undesirable particulate matter such as surgical debris, but must also be freed of entrained air bubbles before being returned to the patient or supplied to an oxygenator.

It is known to provide in a cardiotomy reservoir a filter unit comprising means for screening out particulate matter, and means for defoaming the blood to remove the air trapped therein. Examples of such known devices include those disclosed in U.S. Pat. Nos. 3,507,395 and 3,768,653. U.S. Pat. No. 3,507,395 to Bentley discloses a cardiotomy reservoir comprising a chamber containing a plate surrounded by a fibrous filter element contained in a nylon bag. The plate first spreads the incoming blood to remove air bubbles therefrom which are vented, or drawn by vacuum, from the chamber, and the filter removes solid particles from the blood as it passes therethrough before leaving the chamber. U.S. Pat. No. 3,768,653 to Brumfield discloses a cardiotomy reservoir comprising a tubular chamber having a tangential inlet for the blood which is directed onto a filter across one end of the chamber which also contains a conical air filter.

Many other filtration systems are known for filtering blood and many use multiple layer elements to remove unwanted materials from the blood as it passes through the layers. U.S. Pat. No. 3,765,536 and U.S. Pat. No. 3,765,537 to Rosenberg disclose a multiple layer blood filter elements including one comprising a first layer of coarse polypropylene netting, a second downstream layer of open-mesh polyester, a third spacer layer of polypropylene netting, a fourth microporous layer and a fifth polypropylene netting spacer layer.

Other commercially available reservoirs contain various arrangements of defoamer and filter layers. However, the known arrangements suffer from the disadvantage of having a limited useful life before one or more of the layers, particularly the filter layers becomes blocked or obstructed. We have now discovered an arrangement whereby the useful lifetime of the cardiotomy reservoir may be extended beyond that hitherto possible without significant blockage or obstruction in normal use and which more efficiently separates entrained gas and particulate matter from the blood.

SUMMARY OF THE INVENTION

According to the invention there is provided a blood filter device suitable for use in a cardiotomy reservoir, which comprises:
  a depth filter media layer; and
  a fine pore size, screen filter layer;
said screen filter layer being downstream of and separated from said depth filter layer by at least one intermediate spacer layer.

Preferably, the filter device of the invention is a defoamer/filter unit suitable for use in a cardiotomy reservoir, which comprises:
  a first, inner tubular member of porous sponge material for removing gas bubbles from blood directed onto the inner surface of said tubular member;
  a second tubular member in close proximity or in contact with and surrounding said first member and formed of depth filter media to provide a first stage filter site for particulate matter in the blood;
  a third tubular member of porous sponge material in close proximity or in contact with and surrounding said second tubular member and for providing a porous spacing between said second member and a downstream second stage filter comprising:
  a fourth tubular member of fine filter screen in close proximity or in contact with and surrounding said third tubular member, and for removing substantially all remaining undesirable particulate matter in said blood.

In another embodiment, the invention also provides a cardiotomy reservoir incorporating the filter device of the invention.

Thus the invention also provides a combined cardiotomy defoamer, filter and reservoir device for removing air bubbles and undesirable particulate matter from blood evacuated from a surgical field said device accomodating substantial blood flow for extended periods of time with minimal increase in pressure between the blood inlet and outlet of said device, comprising:
  a first annular tube of reticulated porous sponge material treated with antifoam compound for removing gas bubbles from said blood;
  a second annular tube of a nonwoven depth filter media surrounding and closely proximate said first annular tube for providing a first stage filter for larger particulate matter;
  a third annular tube of reticulated porous sponge material untreated with any antifoam material surrounding and closely proximate said second annular tube for providing a porous spacing between the external surface of said second annular tube and a downstream second stage filter to provide multiple fluid paths between the exterior surface of said first stage filter and said second stage filter;
  a fourth annular tube of a filter media surrounding and closely proximate said third annular tube for removing substantially all remaining undesirable particulate matter; and
  a generally hollow housing surrounding said first, second, third and fourth annular elements and having said blood inlet in communication with the interior of said first annular tube, a reservoir chamber for receiving the filtered blood after it has been filtered through said fourth annular tube, an air vent for venting air separated from the blood in said device; and said blood outlet in communication with said reservoir chamber.

This invention also provides a filter for a cardiotomy reservoir comprising a final stage screen filter having a substantially uniform pore size, preferably selected from the range of from about 20 to 60 microns.

In the invention, the depth filter material is preferably treated with a wetting agent, such as a polyol. This provides unexpectedly rapid flow and wetting in the depth filter and contributes to the efficiency of the device.

By spacing apart the depth filter and screen filter layers and interposing between them at least one spacer layer, filtering efficiency and the useful lifetime of the filter device of the invention is improved. In this arrangement, obstruction of the screen filter by filtered particles and air bubbles in an adjacent depth filter layer is avoided and obstruction of an escape route for air bubbles leaving the depth filter by a blood-soaked adjacent screen filter is also avoided, resulting in a free-flowing system that does not exhibit substantial pressure buildup with time, which would be caused by increasing blockages in the filter.

BRIEF DESCRIPTION OF THE DRAWINGS

Embodiments of this invention are illustrated in the accompanying drawings, in which.

DETAILED DESCRIPTION OF THE PREFERRED EMBODIMENT

Figure 3:
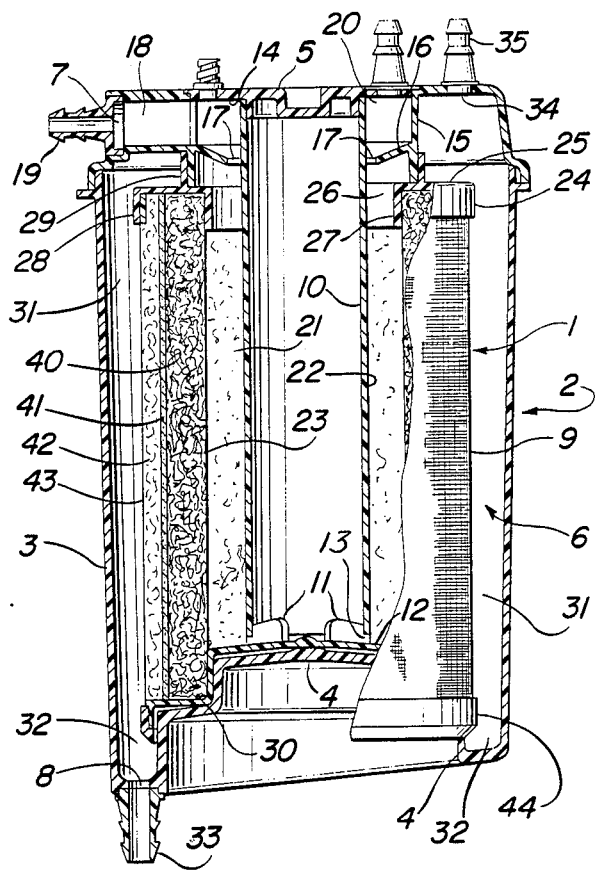
FIG. 3 is a partial cross-sectional view of the reservoir shown in FIG. 1, taken along the line 3—3.

Referring to FIG. 3, there is shown a filter unit 1 according to the invention incorporated in a cardiotomy reservoir 2. Reservoir 2 comprises an outer, substantially cylindrical wall 3 having a base 4 and a top 5 to form within them a reservoir chamber 6. The chamber 6 has an inlet port 7 near its top and an outlet 8 at its bottom. A hollow, tubular defoamer/filter element 9 is arranged along the longitudinal axis of the chamber 6 and is spaced from outer wall 3 in a manner such that all blood entering the reservoir 2 through inlet 7 is caused to flow from the hollow space within the defoamer/filter element 9 through its walls before leaving the chamber through outlet 8.

Figure 1:
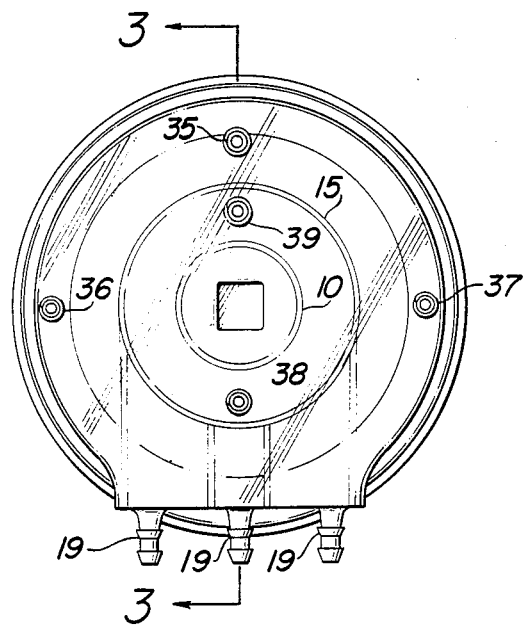
FIG. 1 is a top view of a cardiotomy reservoir according to the invention.
Figure 2:
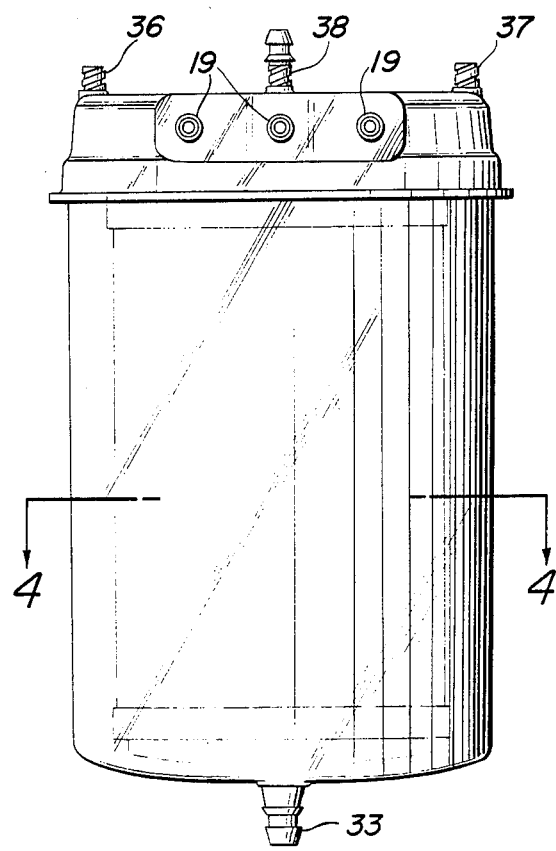
FIG. 2 is a side elevational view of the reservoir shown in FIG. 1.

More particularly, element 9 is arranged around an internal, substantially cylindrical column 10 extending along the central, longitudinal axis of chamber 6 between base 4 and top 5. In the embodiment shown in FIG. 3, the bottom of column 10 is seated upon spacers 11 which project upwardly from a filter base 12 shaped to nest against, and be sealed to, the base 4 of reservoir 2. As can be seen more clearly in FIG. 4, spacers 11 are arranged radially and symmetrically around the longitudinal axis of the chamber and, as shown in Figure 3, separate the bottom of column 10 from the upper surface of filter base 12 thereby creating a space 13 between the bottom end of column 10 and filter base 12. The top of column 10, however, is attached to the inner surface 14 of top 5 without any significant gap between the top of column 10 and surface 14. An annular wall 15 extends downwardly from the inner surface 14 of top 5 and is spaced around and concentric with the upper end of column 10. Part-way down wall 15 an inwardly projecting flange 16 extends part-way towards column 10 so as to leave a gap 17 around column 10. An inlet passage 18 opens through wall 15 above flange 17 and from inlet port 7. Inlet 7 has an external connector 19 for attachment of a tube (not shown) to conduct blood into the reservoir for purification. Usually, as shown in FIGS. 1 and 2, three identical inlet ports 7 are provided with their respective connectors 19. Each inlet 7 has inlet passages 18 to within wall 15. Column 10, wall 15 and the inner surface 14 of top 5 therefore define an annular inlet chamber 20 around column 10 in fluid communication with inlet port 7 and, through gap 17, to an extended, annular inlet passage 21 around column 10 and between the outer surface 22 of column 10 and the inner surface 23 of defoamer/filter element 9.

Element 9 is sealably retained at its upper end in an upper end cap 24 which comprises an end plate 25 having a central orifice 26 around column 10 and bounded by a downwardly projecting, inner annular flange 27. The periphery of plate 25 has a downwardly projecting outer, annular flange 28. The separation of flanges 27 and 28 is such as to snugly accept the thickness of defoamer/filter element 9 which is sealed between those flanges and to the underside of plate 25. On the upper surface of plate 25, between orifice 26 and the periphery of plate 25, an upwardly extending, annular flange 29 surrounds and is sealed to the outer surface of the lower part of wall 15, as shown in FIG. 3. The lower end of defoamer/filter element 9 is sealably retained in an internal, downward annular step 30 in filter base 12.

Thus, blood entering reservoir 2 through inlet 7 and passing into extended inlet passage 21 must travel through defoamer/filter 9 to reach outlet 8 from the reservoir. The outer surface to defoamer/filter 9 is separated from outer wall 3 of the reservoir by a space 31 around defoamer/filter 9. Purified blood leaving defoamer/filter 9 passes down space 31 and is guided to outlet 8 by the base 4 of reservoir 2 forming a trough 32 around and below the base of defoamer/filter 9 as a lower extension of space 31. Trough 32 is angled towards outlet 8 to direct the flow of blood through the outlet. Outlet 8 has a connector 33 for attachment of an outlet tube (not shown). Space 31 around defoamer/filter 9 is in fluid communication with a gas vent 34 through the top 5 of reservoir 2 by means of a chamber between outer wall 3 and annular wall 15. Vent 34 has a connector 35 for attachment of an outlet tube (not shown).

The top 5 of reservoir 2 has further fluid access means. A pair of priming ports 36 and 37 (FIG. 1) provide means for adding fluid to the reservoir without filtration by accessing gap 31 directly. Another pair of priming ports 38 and 39 (FIGS. 1 and 2) provide means for adding fluid to the reservoir with filtration by accessing the annular chamber 20 within wall 15 so that the added fluid will pass into extended inlet passage 21 and through defoamer/filter 9.

Figure 4:
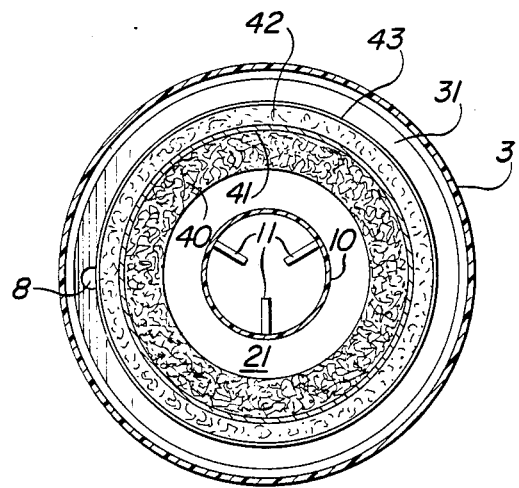
FIG. 4 is a cross-sectional view of the reservoir shown in FIG. 2, taken along the line 4—4.

The defoamer/filter element 9 comprises a series of concentric tubular members, as can be most clearly seen in FIG. 4. Element 9 comprises a first, inner tubular defoamer member 40 whose inner surface 23 defines with central column 10 the vertical confines of the extended annular inlet passage 21. Around defoamer 40 is a second tubular member 41 serving as a depth filter which is surrounded by a third tubular member 42 serving as a spacer which in turn is surrounded by a fourth tubular member 43 serving as a screen filter. The adjacent surfaces of members 40, 41, 42, and 43 are in close proximity and are preferably in contact with one another to form a substantially continuous, layered structure.

Defoamer member 40 comprises an open cell, blood compatible, synthetic polymeric foam material to collapse blood foam as the blood begins to pass through defoamer/filter element 9. Defoamer 40 is preferably formed of a thermally reticulated polyurethane foam having, for example, about a 20 pore per inch size. Preferably, defoamer 40 is treated with a medical antifoam agent to assist the defoaming step. Suitable antifoam agents include silicone antifoams such as Antifoam A available from Dow Chemical Company. Defoamer 40 is preferably formed from a sheet of foam about 6½ inches high and about 12 inches wide to fit a typical reservoir having a capacity of about 2 liters. The two opposite upright shorter sides are joined together to form the tubular member and the longitudinal seam formed by the join is sealed by radio frequency welding.

Depth filter 41 comprises a synthetic non-woven material such a polypropylene or a polyester and provides a system of complex pathways as a first stage filter for particulate matter in the blood. While defoamer layer 40 will act as a gross filter to prevent passage of large debris carried by the blood, such as bone chips and tissue fragments, filter 41 more effectively filters and prevents passage of smaller particles in the blood through element 9. Preferably, filter 41 has a mean pore diameter of about 50 microns and a maximum pore diameter of about 90 microns. Filter 41 is also preferably made up from about 80% 3 denier fiber and about 20% 1.8 denier fiber and callendared to produce a fabric having a weight of about 8 ounces/sq. yard. Preferably, the outer side of filter 41 has a relatively smooth callendared surface and the inner side has a fluffy surface to increase the effective area of the inner surface of the filter which is first exposed to the blood and to better filter gradually the particulate matter without becoming clogged. Filter 41 should wet well and therefore is not treated with antifoam agent but is preferably treated with a small amount of wetting agent. In a typical wetting treatment procedure, the fabric is cut to an appropriate sheet size, usually about 6½ inches high and about 13 inches wide dry cleaned and heat sealed along its edge. The fabric is washed with a cleaning agent in pyrogen-free water and rinsed. After washing and while still damp, the fabric is treated with a solution of polyol wetting agent in pyrogen-free water and thoroughly dried. The final fabric should preferably exhibit thorough wetting when hydrostatically tested at 4.0+1.0 inches of water. The two opposite shorter sides of the fabric are joined together to form the tubular member and the seam is sealed by impulse welding.

Spacer 42 comprises a synthetic foam material similar or identical to that of defoamer 40 but having a larger pore size, usually about double the pore size of defoamer 40, for example about 10 pore per inch foam. Spacer 42 is preferably prepared in the same manner as that described for defoamer 40. In normal manufacture, the first three layers of element 9 consisting of defoamer 40, depth filter 41 and spacer 42 are assembled in their proper order, one around the other and sealed by hot melt glue at their bottom edges to filter base 12. Outer screen filter 43 is pulled over the assembly and sealed to filter base 12 between base 12 and a retaining ring 44 (FIG. 3). The top of the completed defoamer/filter element 9 is then sealed to upper end cap 24 between flanges 27 and 28 and plate 25.

Spacer 42 separates depth filter 41 from the outer layer of the defoamer/filter element 9, which is formed by the screen filter 43. Filter 43 comprises a thin layer of blood compatible, synthetic material having a small, defined pore size. Preferably, filter 43 is formed from a woven polyester fabric. On the scale described above for the other components of the defoamer/filter element 9, filter 43 is preferably formed from a piece of fabric about 13½ inches wide and about 6½ inches high. The two opposite shorter sides are sewn together and the filter assembled with the remainder of the element 9 as described above. For optimum filtering, filter 43 should have a pore size preferably no less than about 20 microns, for example about 43 microns, and preferably less than 60 microns. Preferably, defoamer/filter assembly 9 is at least about 90% effective in removing from the blood material having a size greater than or equal to about 20 microns.

In use, blood is supplied to reservoir 2 either by a pump (not shown) in the inlet line or by a vacuum pump (not shown) applying suction to reservoir 2. The blood enters the reservoir 2 through inlet port 7 and inlet passage 18 to inlet chamber 20. Then the blood spills over flange 16 through gap 17 and into the extended inlet passage 21. Preferably, flange 16 is angled downwardly, as shown in FIG. 3, to direct the blood against the outer surface 22 of column 10. This encourages the blood to cascade down column 10 and tends to minimize splashing and excess foam formation while providing an extended surface area of blood to encourage release of larger air bubbles entrained in the blood. The blood then travels across gap 21 between column 10 and defoamer 40 and enters defoamer 40 where the blood foam is collapsed and substantially all the air bubbles remaining in the blood are separated out before the blood passes into depth filter 41 for removal of particulate matter therefrom. The following spacer layer 42 prevents the blood and any air bubbles leaving filter 41 from obstructing each other and provides separate pathways for gas and blood through the open structure of spacer layer 42. If the spacer 42 was omitted any air bubble leaving depth filter 41 would tend to obstruct the adjacent portion of screen filter 43 and hinder or prevent passage of blood through that portion of screen 43. Similarly, blood leaving depth filter 41 would tend to form a film in screen filter 43 and form a barrier to any air bubble about to leave filter 41, thereby obstructing that portion of filter 41 against passage of blood. Moreover, particulate matter trapped by filter 41 near its outer, downstream surface would also tend to block the adjacent portion of screen filter 43 to passage of blood through the screen.

This spacer 42 provides improved flow of fluid through the defoamer/filter element 9 and reduces blockage in comparison to prior art devices, thereby extending the useful life of the reservoir and avoiding pressure buildup caused by blockages and which can damage the blood.

When blood flows down the outside of screen filter 43, spacer 42 prevents air in the lower part of the filter device from becoming trapped there by that blood. Gas is free to escape up the spacer layer to exit through the filter device near its top into space 31 around the filter device and escape the reservoir 2 through vent 34.

This unexpectedly effective design according to the invention which allows extended use of the reservoir and avoids pressure buildups, is evidenced by the following data which describe a rigorous test in which pressure in the device, as measured at the inlet, remains unusually constant even over extended periods of time.

The precise reasons for the unexpected results achieved with the device of this invention and its mode of operation are not completely understood at the present time. The mode of operation and results described herein are based upon the present understanding of the invention.

Six (6) liters of fresh heparinized bovine blood, adjusted to a 35% hematocrit and an ACT (activated clotting time) of 420 seconds (±20 sec), was recirculated at 1 LPM (liters per minute) for three (3) hours through each unit. Room air was pumped through the unit at 1 LPM along with the blood. The temperature of the blood was ambient room temperature (23° C.±2° C.). The inlet pressure was monitored at the priming port site (through the defoamer).

Usually, the reservoir of the invention does not show a significant increase in pressure with relation to time, as shown in Table 1.

TABLE 1

| Time (Hours) | Average Inlet Pressure (mmHg) |
| --- | --- |
| 1 | 2.0 |
|   | (0.0–3.0) |
| 2 | 3.0 |
|   | (0.0–4.0) |
| 3 | 3.0 |
|   | (0.0–4.0) |
| N = 4 |   |

*N = # of tests

We claim:

1. A combined cardiotomy defoamer, filter and reservoir device for removing air bubbles and undesirable particulate matter from a surgical field said device accommodating substantial blood flow for extended periods of time with minimal pressure increase in said device between the blood inlet and outlet of said device, comprising:
    a first annular tube of reticulated porous sponge material treated with anti-foam compound for removing gas bubbles from said blood;
    a second annular tube of a non-woven depth filter media surrounding and directly adjacent said first annular tube for providing a first stage filter for larger particulate matter;
    a third annular tube of a reticulated porous sponge material untreated with any anti-foam material surrounding and closely proximate said second annular tube for providing a porous spacing between the external surface of said second annular tube and a downstream second stage filter to provide multiple fluid paths between the exterior surface of said first stage filter and said second stage filter;
    a fourth annular tube surrounding and closely proximate said third annular tube, said fourth annular tube comprised of a screen filter having a sufficiently small pore size to enhance the filtration efficiency of the first stage filter by trapping substantially all remaining undesirable particulate matter;
    said third annular tube of reticulated porous sponge material having a pore size greater than the pore size of both said second and fourth annular tubes; and
    a generally hollow housing surrounding said first, second, third and fourth annular elements, said housing and annular elements sharing a common vertically oriented longitudinal axis, said blood inlet extending through an upper end of said housing and in communication with the interior of said first annular tube, an annular reservoir chamber surrounding said fourth annular tube for receiving the filter blood after it has been filtered through said fourth annular tube, an air vent located at said housing upper end for venting air separated from the blood in said device; and said blood outlet located at a lower end of said housing and in communication with said reservoir chamber.

2. The combined cardiotomy defoamer, filter and reservoir device of claim 1 wherein said second annular tube provides a wide, range of non-uniform pore sizes.

3. The combined cardiotomy defoamer, filter and reservoir device of claim 2 wherein said second annular tube has a maximum pore size of approximately 90 microns and a mean pore size of approximately 50 microns.

4. The combined cardiotomy defoamer, filter and reservoir device of claim 1 wherein said fourth annular tube provides a screen filter of well defined, substantially uniform pore size.

5. The combined cardiotomy defoamer, filter and reservoir device of claim 4 wherein said pore size of said fourth annular tube is selected from the range of about 20 to 60 microns.

6. The combined cardiotomy defoamer, filter and reservoir device of claim 1 wherein said second annular tube has a fuzzy exterior surface proximate the exterior surface of said first annular tube for providing a larger surface area for blood exiting the defoamer material and for initally capturing the larger particulate matter in said fuzzy material.

7. The combined cardiotomy defoamer, filter and reservoir device of claim 1 wherein said second annular tube is treated with a suitable wetting agent.

8. The combined cardiotomy defoamer, filter and reservoir device of claim 1 in which said first annular tube is formed of material having approximately 20 pores per inch.

9. The combined cardiotomy defoamer, filter and reservoir device of claim 1 wherein said third annular tube of reticulated porous sponge material is formed of material having approximately 10 pores per inch.

10. The apparatus of claim 1 wherein said third annular tube of reticulated porous sponge material has a thickness which is greater than the thickness of said annular tube of nonwoven depth filter media.

11. A combined cardiotomy defoamer, filter and reservoir device for removing air bubbles and undesirable particulate matter from blood evacuated from a surgical field, said device accommodating substantial blood flow for extended periods of time with minimal pressure increase in said device between the blood inlet and outlet of said device, comprising:
    first means for removing gas bubbles from said blood;
    second means directly adjacent and downstream of said first means formed of a depth filter media for providing a first stage blood filter;
    third means downstream of said second means for providing a porous spacing between the external surface of said second means and a downstream second stage blood filter, fourth means downstream of said third means providing a second stage blood filter which has a sufficiently small pore size so as to enhance the filtration efficiency of the first stage filter by substantially removing remaining undesirable particulate matter which has not been removed by said first stage filter, said third stage having a pore size greater than both said second and fourth means, said third stage preventing proximal contact between said first stage blood filter and said second stage blood filter so that (i) separate fluid paths are provided for gas and blood to inhibit any blockage of said second stage filter by air bubbles, and (ii) multiple fluid paths are provided between said first stage filter and said second stage filter such that particulate matter entrapped in either said first stage filter to said second stage filter will not block out an abutting portion of the other said filter stages, and a housing surrounding said first, second, third, and fourth means and having said blood inlet in communication with the upstream side of said first means, a reservoir chamber for receiving the filtered blood downstream of said fourth means, an air vent for venting air separated from blood in said device and said blood outlet in communication with said reservoir chamber.

12. The combined cardiotomy defoamer, filter and reservoir device of claim 11 wherein said second means provides a wide range of non-uniform pore sizes.

13. The combined cardiotomy defoamer, filter and reservoir device of claim 12 wherein said first stage blood filter has a maximum pore size of approximately 90 microns and a means size of approximately 50 microns.

14. The combined cardiotomy defoamer, filter and reservoir device of claim 11 wherein said fourth means is formed of a screen media of well defined, substantially uniform pore size.

15. The combined cardiotomy defoamer, filter and reservoir device of claim 14 wherein said screen media has a pore size selected from the range of about 20 to 60 microns.

16. The combined cardiotomy defoamer, filter and reservoir device of claim 11 wherein said second means has a fuzzy exterior surface proximate the exterior surface of said first means for providing a larger surface area for blood exiting said defoamer means and for initially capturing the larger particulate matter.

17. The combined cardiotomy defoamer, filter and reservoir device of claim 11 wherein said first stage filter media is treated with a suitable wetting agent.

18. The apparatus of claim 11 wherein said third means has a thickness which is greater than the thickness of said second means.

19. A combined cardiotomy defoamer, filter and reservoir device for removing air bubbles and undesirable particulate matter from blood evacuated from a surgical field, said device accommodating substantial blood flow for extended periods of time with minimal pressure increase in said device between the blood inlet and blood outlet of said device, said device comprising:

a substantially hollow housing having an upper and a lower end, said blood inlet extending through said upper end, said blood outlet extending through said lower end;

a substantially vertically oriented column within said housing, the exterior of said column being substantially imperforate;

a defoamer element comprised of an annular tube of porous sponge material treated with anti-foam compound for removing gas bubbles from said blood, said defoamer surrounding and spaced from said column so as to define an annular space therebetween, said space in fluid communication with said blood inlet so that blood entering said space cascades down the exterior of said column so as to release larger air bubbles entrained in the blood;

an annular first stage filter element surrounding and directly adjacent to said defoamer element, said first stage filter element trapping larger particulate matter;

an annular porous spacer element surrounding said first stage filter element for providing a porous spacing between the external surface of said first stage filter and a downstream second stage filter to provide multiple fluid paths between the exterior of first stage filter and said second stage filter;

an annular second stage filter element surrounding said spacer element, said second stage filter having a sufficiently small pore size to enhance the filtration efficiency of the first stage filter by trapping substantially all remaining undesirable particulate matter;

said spacer element having a greater pore size than the pore size of both said first and second stage filter elements;

a reservoir chamber between said second stage filter and said housing for receiving the filtered blood after it has been filtered through said second stage filter, said blood outlet in communication with said reservoir chamber; and an air vent located at said housing upper end for venting air separated from the blood in said device.

20. The device of claim 19 wherein the pore size of said spacer element is greater than the pore size of said defoamer element.

21. The device of claim 19 wherein said first stage filter comprises a depth filter.

22. The device of claim 19 wherein said second stage filter comprises a screen filter.

23. The device of claim 19 wherein said spacer element comprises a reticulated porous sponge material untreated with any anti-foam material.

24. The device of claim 19 wherein said column has a substantially cylindrical exterior.

* * * * *